United States Patent
Barad

[19]

[11] Patent Number: 5,822,037
[45] Date of Patent: Oct. 13, 1998

[54] AUTOMATED DARK ADAPTOMETER

[75] Inventor: James P. Barad, Burkburnett, Tex.

[73] Assignee: The United States of America as represented by the Secretary of the Air Force, Washington, D.C.

[21] Appl. No.: 909,362

[22] Filed: Aug. 11, 1997

[51] Int. Cl.⁶ .................................................. A61B 3/02
[52] U.S. Cl. ........................................ 351/224; 351/246
[58] Field of Search .................................. 351/222, 224, 351/226, 246

[56] References Cited

U.S. PATENT DOCUMENTS

| 5,079,232 | 1/1992 | Obsawa et al. | 514/25 |
| 5,080,478 | 1/1992 | O'Brien et al. | 351/224 |
| 5,461,435 | 10/1995 | Rootzen et al. | 351/224 |

*Primary Examiner*—Huy Mai
*Attorney, Agent, or Firm*—Stanton E. Collier

[57] ABSTRACT

The present invention modifies the Goldmann-Weeker's dark adaptometer so that all testing may be done automatically and analysis of the data may be completed in a rapid manner and further varied. The automated dark adaptometer is composed of the standard Goldmann-Weeker's dark adactometer having the traditional Ganzfeld bowl attached thereon. A computer acting through a computer interface is connected to a stepper motor and shaft encoder. The stepper motor is connected to the light control knob of the dark adaptometer. The patient being tested inputs responses to a patient signaling switch which is connected to the computer interface. The computer has a program has a specialized program therein for controlling the change in light intensity, recording this change, recording the patients response thereto and any other desired variables.

3 Claims, 2 Drawing Sheets

AUTOMATED DARK ADAPTOMETER

STATEMENT OF GOVERNMENT INTEREST

The invention described herein may be manufactured and used by or for the Government for governmental purposes without the payment of any royalty thereon.

BACKGROUND OF THE INVENTION

The present inventor relates to medical devices used in testing of human beings, and, in particular, relates to testing of eyes.

The Goldmann-Weeker's dark adaptometer is a medical testing instrument designed to measure the functions of the retinal photoreceptors. It has been in existence since about 1950 and since that time, the instrument has not been changed or the testing methods used therewith.

The current method of testing dark adaptation, using the Goldmann-Weeker's device, is as follows: A patient is seated in a darkened room with his chin resting on the rim of a Ganzfeld bowl mounted to the front of the instrument. The untested eye is patched over and a bright light is turned on for five minutes to bleach the retinal photoreceptors of the unpatched eye. The light is then turned off and the patient is asked to look at a dim red light near the center of the reflective bowl. The technician, seated at the opposite end of the instrument, then turns a control knob which increases the intensity of the light projected onto a small screen at the center of the bowl. When the patient can first detect the light, he knocks on the table and the technician pulls back on the control knob, perforating a piece of graph paper attached to a rotating drum at the top of the instrument. The technician then decreases the light intensity by rotating the control knob counterclockwise, waits 5 to 15 seconds, then once again increases the light intensity. This cycle is continued for 45 minutes and then is repeated in the other eye. Once the test is completed, the graph paper is removed from the drum and each of the perforations is accentuated with ink, yielding a dark adaptation curve.

This manual method requires the technician to remain in the room with the patient throughout the entire examination, administering a tedious, labor-intensive test and then meticulously prepare a graph before the data can be interpreted. Because the technician directly controls the rate and interval over which the light intensity is changed, a large amount of interoperator variability exists. Furthermore, because the data is recorded in "hard-copy" form, any additional manipulation is prohibitively time-consuming.

Thus, there exists a need for a improved dark adaptometer.

SUMMARY OF THE INVENTION

The present invention modifies the Goldmann-Weeker's dark adaptometer so that all testing may be done automatically and analysis of the data may be completed in a rapid manner and further varied.

The automated dark adaptometer of the present invention is composed of the standard Goldmann-Weeker's dark adaptometer having the traditional Ganzfeld bowl attached thereon. A computer acting through a computer interface is connected to a stepper motor and shaft encoder. The stepper motor is connected to the light control knob of the dark adaptometer. The patient being tested inputs responses to a patient signaling switch which is connected to the computer interface. The computer has a program has a specialized program therein for controlling the change in light intensity, recording this change, recording the patients response thereto and any other desired variables.

Therefore, one object of the present invention is to provide an improved Goldmann-Weeker's dark adaptometer.

Another object of the present invention is to provide a Goldmann-Weeker's dark adaptometer that is able to adjust the light intensity according to a specialized program.

Another object of the present invention is to provide a Goldmann-Weeker's dark adaptometer that is able to record all testing information as the patient reacts to the testing program.

Another object of the present invention is to provide a Goldmann-Weeker's dark adaptometer that is able to digitally analysis the testing information produced.

Another object of the present invention is to provide a Goldmann-Weeker's dark adaptometer that requires no human intervention during the testing process.

Another object of the present invention is to provide a Goldmann-Weeker's dark adaptometer that allows for the testing protocols to be customized easily.

Another object of the present invention is to provide a Goldmann-Weeker's dark adaptometer that wherein the data is digitally stored and can be further manipulated using graphing programs.

These and many other objects and advantages of the present invention will be ready apparent to one skilled in the pertinent art from the following detailed description of a preferred embodiment of the invention and the related drawings.

DESCRIPTION OF THE PREFERRED EMBODIMENT

The present invention automates the Goldmann-Weeker's dark adaptometer. A specially programmed computer having an interface module drives a stepper motor connected to the dark adaptometer.

Figure 1:
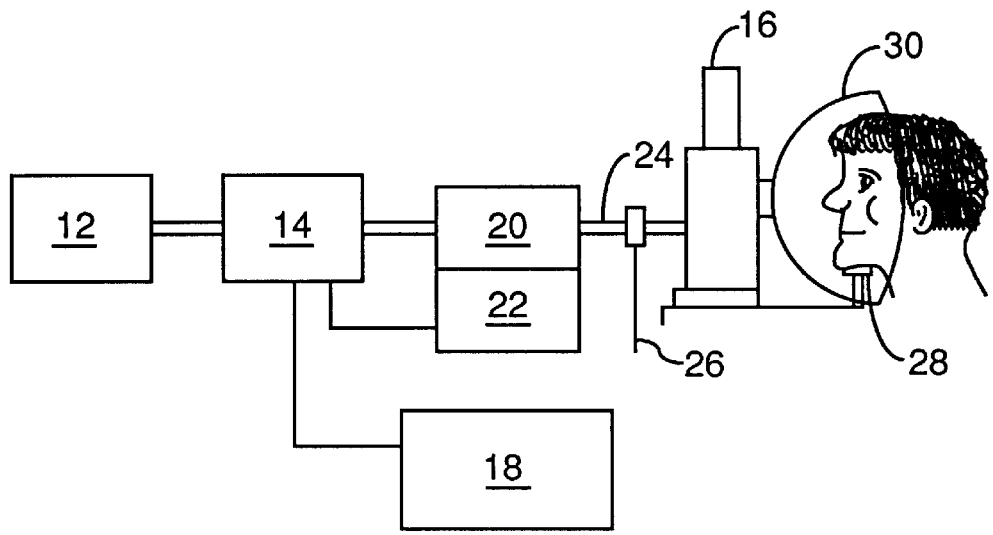
FIG. 1 illustrates the automated dark adaptometer by block diagram.

Referring to FIG. 1, the improved dark adaptometer 10 is shown in block schematic. A computer 12 such as a personal computer (PC) has a specialized program as shown in Table 1 for controlling the improved dark adaptometer 10. The computer 12 is connected to a computer interface 14 that controls of all the functions of a dark adaptometer 16 such as instrument on/off, high-intensity light on/off, variable light intensity control, records elapsed time and patient responses. Further the interface 14 accepts patient responses through a signaling switch 18. The interface 14 also connects to the stepper motor 20 and an absolute shaft encoder 22. The output shaft 24 of the stepper motor 20 connects to the light intensity control 26.

Figure 2:
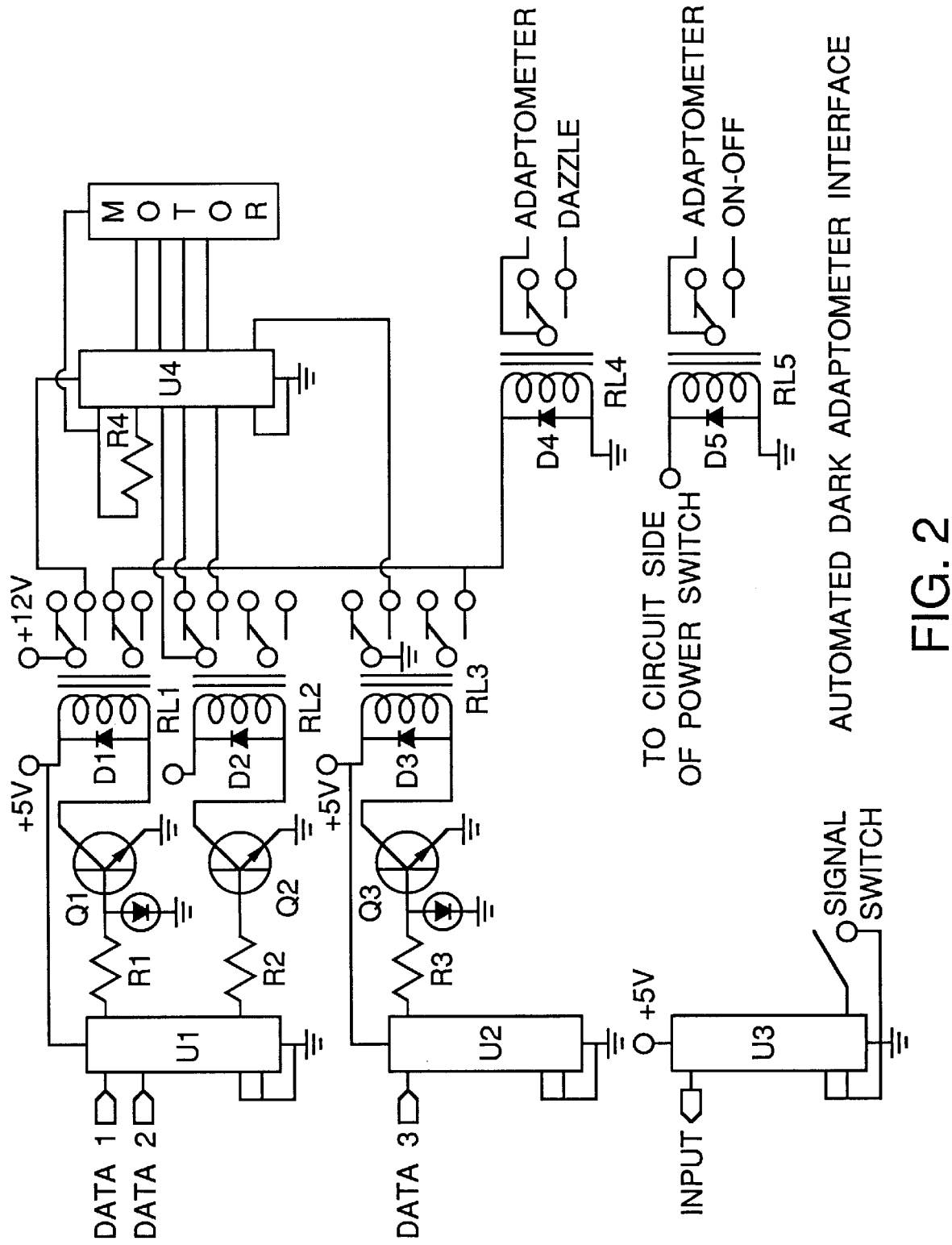
FIG. 2 illustrates by electrical schematic the computer interface used in the present invention.

The method of testing a patient consists of turning on computer 12, loading the computer program noted in Table 1, and entering the patient information. The patient is seated in front of the improved dark adaptometer 10 in a darkened room with his chin on the adjustable chin rest 28 and one eye patched over. The computer begins the examination by resetting its internal clock to zero and illuminating the Ganzfeld bowl 30 with a bright light for five minutes to bleach the retinal photoreceptors of the tested eye. When the five minutes has elapsed, the computer 12 turns the light off. The computer again resets its clock than slowly increases the intensity of the light projected onto a screen at the center of the bowl by initiating forward movement of a stepper motor 20 attached to the control knob 26 of the dark adaptometer 16. When the patient can first detect the light, he presses a trigger switch 18 connected to the computer interface 14. The computer 12 records the elapsed time and the intensity of the light perceived. The light intensity is calculated by measuring the distance of the stepper motor travel from the start of the test from an absolute shaft encoder 22 attached to the stepper motor 20. The intensity is read from a calibration curve previously prepared using a standardized photometer. The computer 12 then decreases the light intensity by reversing the stepper motor 20, waits a random length of time, and then once again increases the light intensity. This cycle is repeated for 45 minutes, in accordance with standard testing methods. Once the test is complete, the data are stored to a disk in a format usable by almost any graphing program, not shown. The electrical schematic for the computer interface 14 is shown in FIG. 2.

Figure 3:
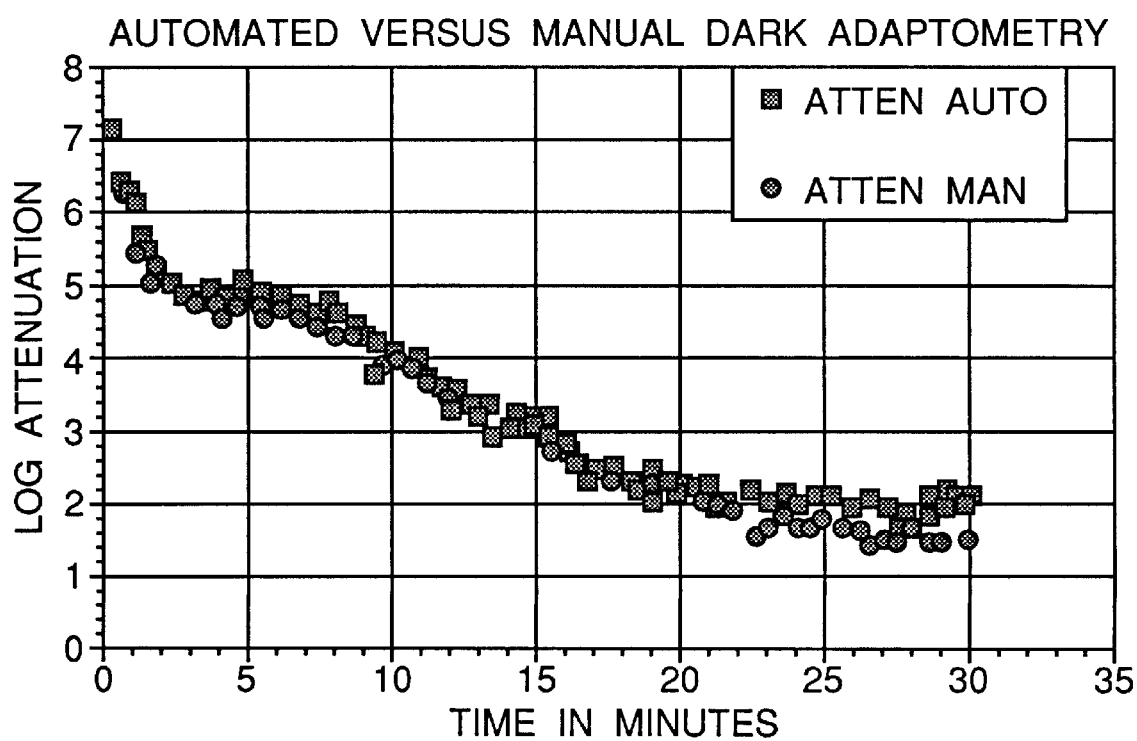
FIG. 3 is an illustration comparing the manual data to the automated data taken by the present invention.

The data obtained by the improved dark adaptometer 10 is shown in FIG. 3 as compared to the manual method.

TABLE 1

EM Automated Dark Adaptometry

```
     TYPE: infodisk
            lname AS STRING * 15
            fname AS STRING * 15
            ssn AS STRING * 14
            test AS STRING * 3
     END TYPE;
     DIM darkinfo As indodisk
     DIM a(500, 2)
     DIM as(500, 2)
     c = 4935:      REM   c = stepper (intensity) counter
     t = 17:        REM   t = motor speed (higher # = slower
                          rate)
     h = 175:       REM   h = trigger code (home = 175,
                          notebook = 168)
     b = 143:       REM   b = base code for interface "ready"
     u = 680:       REM   u = steps equalling one log intensity
                          unit
     si = 250:      REM   si = decrease amount to start intensity
     pct = .85:     REM   pct = percent of intensity after signal
     st$ = "00:00:00":  REM   st$ = start time for each test unit
     light$ = "00:05:00":  REM  light$ = bleaching time
     warn$ = "00:04:55":  REM  warn$ = time "warning to start"
                          will be given
10   OUT 890, 2:    REM   Turns motor driver off
     OUT 888, 128:  REM   Opens stepper relay
     i = INP(889)
     IF i <> b THEN 60000
30   CLS
     LOCATE 7, 29: PRINT "Enter patient data:"
     LOCATE 9, 29: LINE INPUT "Last name:   "; l$
     LOCATE 10, 29: LINE INPUT "First name:   "; F$
     LOCATE 11, 29: LINE INPUT "Identifier (SSN):   "; s$
     LOCATE 14, 26: PRINT "Is the information correct!?
50   i$ = UCASE$(INKEY$)
     IF i$ = "Y" THEN 60
     IF i$ = "N" THEN 30
     GOTO 50
60   CLS
     LOCATE 8, 28: PRINT "Select testing protocol:"
     LOCATE 10, 34: PRINT "1) Yates'"
     LOCATE 11, 34: PRINT "2) Standard"
     LOCATE 12, 34: PRINT "3) Custom"
70   i$ = INKEY$
     pt = VAL(i$)
```

TABLE 1-continued

EM Automated Dark Adaptometry

```
     IF i$ = "1" OR i$ = "2" OR i$ = "3" THEN 100
     GOTO 70
100  y = 0: pl = 0
110  IF i$ = "1" THEN 120
     IF i$ = "2" THEN 130
     IF i$ = "3" THEN 200
120  REM Variables for Yates' protocol
     os$ = "LEFT"
     side$ = "OD"
     fside$ = "RIGHT"
     m = 15
     test = 60
     os$ = "LEFT"
     side$ = "OD"
     fside$ = "RIGHT"
     m = 15
     test = 180: REM 180=45 MIN 3=5 MIN
     GOTO 305
200  CLS
     LOCATE 8, 20: PRINT "(R)ight eye / (L)eft eye / E(X)it ? ";
220  side$ = UCASE$(INKEY$)
     IF side$ = "X" THEN GOTO 70000
     IF side$ = "R" THEN side$ = "OD": GOTO 250
     IF side$ = "L" THEN side$ = "OS": GOTO 260
     GOTO 220
250  os$ = "LEFT"
     GOTO 270
260  os$ = "RIGHT"
     GOTO 270
270  LOCATE 10, 20: LINE INPUT "Set testing interval (minutes): ";
            step$
     IF step$ = " " GOTO 200
     m = (VAL(Step$) * 60)
300  LOCATE 12, 25: LINE INPUT "Set number of tests: "; test$
     IF test$ = " " GOTO 300
     test = VAL(test$)
305  CLS
     file$ = LEFT$(l$; 3) + LEFT$(F$; 1) + LEFT$(s$, 2) + ".inf"
     data$ = LEFT$(file$, 6) + side$ + ".x1"
     OPEN file$ FOR RANDOM AS #1
         darkinfo.lname = l$
         darkinfo.fname = F$
         darkinfo.ssn = s$
         darkinfo.test = STR$(test)
     PUT #1, 1, darkinfo
     CLOSE #1
310  CLS
     LOCATE 8, 20: PRINT "'Zero' instrument at maximum intensity"
     LOCATE 10, 27: PRINT "Cover patient's "; os$; "eye"
     LOCATE 14, 26: LINE INPUT "Press < ENTER > when ready";
         q$
     CLS
     LOCATE 10, 14: PRINT "Please standby - decreasing intensity
     to start point"
     LOCATE 12, 30: PRINT "Count down ="
     OUT 890, 1: REM Turns: motor driver on
     FOR s = 1 TO si: REM Decreases intensity to start point
         c = c - 1
         OUT 888, 129
         GOSUB 4000
         OUT 888, 128
         GOSUB 4000
         LOCATE 12, 44: Print c
     NEXT s
     OUT 888, 128
     OUT 890, 2
320  CLS
     CLS
     TIME$ = "00:00:00"
     OUT 888, 129
330  IF TIME$ = warn$ THEN GOSUB 10000
     IF TIME$ = light$ THEN 340
         LOCATE 10, 28: PRINT "*** Bleaching "; side$; " ***"
         LOCATE 12, 27: PRINT "Elapsed time = "; TIME$
         GOTO 330
340  OUT 888, 128
400  CLS
```

TABLE 1-continued

EM Automated Dark Adaptometry

```
     REM LOCATE 12, 26: LINE INPUT "Press <ENTER> to begin
        test"; i$
     OUT 890, 1
 500 CLS
     TIME$ = st$
     TIMER ON
 900 CLS
1000 OUT 888, 1: REM Steps motor forward 0.45 degrees
     GOSUB 4000
     OUT 888, 16: REM Resets parallel port
     GOSUB 4000
1400 i = INP(889): REM Patient response trigger
     c = c + 1: REM "Intensity" counter - up
     GOSUB 6000
     LOCATE 6, 28: PRINT "Testing "; fside$; " eye"
     LOCATE 9, 25: PRINT "Test number = "; (y + 1); " of "; test
     LOCATE 13, 29: PRINT "Intensity = "; c
     d = c
     IF i = h THEN GOTO 2000: REM home i = 175 notebook i = 8
     IF c >=4800 THEN GOTO 2000: REM 70000
     GOTO 1000
2000 SOUND 800, 1
     a$(y, 1) = RIGHT$(TIME$, 5)
     a$(y, 2) = STR$(c)
2100 c = c - 1: REM "Intensity" counter - down
     OUT 888, 129: REM Steps motor backward 0.45 degrees
     GOSUB 4000
     OUT 888, 128: REM Resets parallel port
     GOSUB 4000
     GOSUB 6000
     LOCATE 13, 29: PRINT "Intensity = "; c
     LOCATE 9, 25: PRINT "Test number 32 "; *y + 1); " of "; test
     IF c <> INT(d * pct) THEN 2100
2200 p$ = STR$(TIMER)
     q$ = LEFT$(p$, 5)
     p2 = VAL(q$)
     IF (p2 - p1) >= m GOTO 3100
     GOSUB 6000
     GOTO 2200
3000 STOP
3100 p1 = p2
     y = y + 1
```

Clearly many modifications and variations of the present invention are possible in light of the above teachings and it is therefore understood, that within the inventive scope of the inventive concept, that the invention may be practiced otherwise than specifically claimed.

What is claimed is:

1. An improved dark adaptometer, the improvement to the Goldmann-Weeker's dark adaptometer comprising:

a computer having a program loaded therein for controlling the operation of the Goldmann-Weeker's dark adaptometer;

a computer interface connected to said computer;

a signaling switch connected to said computer interface, said signaling switch for use by a patient under test;

a stepper motor connected to said computer interface having stepper motor drivers therein, said stepper motor having an output shaft being connected to a light intensity control knob of said Goldmann-Weeker's dark adaptometer; and a stepper motor shaft encoder connected to said stepper motor and to said computer interface, said encoder providing shaft movement information to said computer interface.

2. An improved dark adaptometer as defined in claim 1 wherein said computer is a PC.

3. A method for testing functions of retinal photoreceptors of human eyes, said method comprising the steps of:

seating a patient at an improved dark adaptometer and having the patient place his chin in a chin rest in a Ganzfeld bowl after one eye is patched over and a tested eye is left uncovered;

turning on a computer having a program therein for operating the dark adaptometer;

illuminating the Ganzfeld bowl with a bright light for five minutes to bleach the retinal photoreceptors of the tested eye;

turning off the light after a designated time period;

increasing slowly the intensity of the light projected onto a screen at the center of the Ganzfeld bowl by initiating forward movement of a stepper motor attached to a light intensity control knob;

upon detecting the light, the patient presses a trigger switch;

calculating and storing an elapsed time between a start of increasing slowly the intensity of the light and the detecting of the light and the intensity of the light perceived by the computer;

decreasing the light intensity by reversing a stepper motor;

waiting a random time;

repeating the above steps for a designated length of time in accordance with standard testing methods;

repeating these steps for the other eye if so desired; and storing the data.

* * * * *